United States Patent [19]

Chappell et al.

[11] Patent Number: 5,256,405
[45] Date of Patent: Oct. 26, 1993

[54] HERBAL DEODORANT

[75] Inventors: Katherine C. Chappell, Kennebunk, Me.; Pamela A. Scheeler, Portsmouth, N.H.; Gary Rittershaus, Kennebunkport, Me.

[73] Assignee: Tom's of Maine, Kennebunk, Me.

[21] Appl. No.: 814,569

[22] Filed: Dec. 30, 1991

[51] Int. Cl.$^5$ .......................... A61K 7/32; A61K 35/82
[52] U.S. Cl. ................................... 424/65; 424/195.1; 424/DIG. 5
[58] Field of Search .................. 424/65, 401, 195.1, 424/DIG. 5

[56] References Cited

U.S. PATENT DOCUMENTS

| | | | |
|---|---|---|---|
| 4,002,775 | 1/1977 | Kabara | 424/312 |
| 4,014,995 | 3/1977 | Juliano | 424/71 |
| 4,067,977 | 1/1978 | Hoover et al. | 424/246 |
| 4,067,997 | 1/1978 | Kabara | 424/49 |
| 4,759,924 | 7/1988 | Luebbe et al. | 424/65 |
| 4,883,651 | 11/1989 | Meyer | 424/47 |
| 4,921,694 | 5/1990 | Hoppe | 424/47 |
| 4,933,177 | 6/1990 | Grollier | 424/70 |
| 5,137,717 | 8/1992 | Wixforth | 424/78.07 |

FOREIGN PATENT DOCUMENTS

| | | |
|---|---|---|
| 0376761 | 7/1990 | European Pat. Off. . |
| 2351864 | 10/1973 | Fed. Rep. of Germany . |
| 2351927 | 10/1973 | Fed. Rep. of Germany . |
| 2354517 | 10/1973 | Fed. Rep. of Germany . |
| 1475226 | 6/1977 | United Kingdom . |
| 1590485 | 6/1981 | United Kingdom . |
| 1596791 | 8/1981 | United Kingdom . |
| 0077047A1 | 4/1983 | World Int. Prop. O. . |
| 0433911A1 | 6/1991 | World Int. Prop. O. . |

OTHER PUBLICATIONS

Cosmetochem Product Information article, Deo-Usnate, Dr. Marina Fontana, Apr. 1974.
Cosmetic and Drug Preservation, Principles and Practice, edited by Jon J. Kabara, 1984.

Primary Examiner—Thurman K. Page
Assistant Examiner—Sally Gardner
Attorney, Agent, or Firm—Fish & Richardson

[57] ABSTRACT

A stick deodorant composition that has active antibacterial constituents consisting essentially of natural materials, and that is essentially free of petroleum derived constituents and alcohols. In the preferred embodiment, the active antibacterial constituents consist essentially of about 1% to 6% (by weight) Lichen Extract, about 0.1% to 3% Coriander Oil; and about 0.1% to 0.6% Glyceryl Monolaurate.

26 Claims, No Drawings

HERBAL DEODORANT

BACKGROUND OF THE INVENTION

The invention relates to a stick deodorant composition employing only natural bactericides for personal use.

To be effective, a personal deodorant must, of course, reduce odor. It is known that odor in the axillary vault is caused by bacteria metabolizing the rich supply of proteins and lipids supplied by the apocrine sweat glands. The bacterial flora bound in the human axilla (or armpit) that are responsible for odor generation have been identified as gram positive lipophilic diphtheroids and micrococci. The diphtheroids produce the typical pungent axillary odor and the micrococci produce a sweaty isovaleric acid type odor. The moisture and minerals secreted by the eccrine sweat glands serve to enrich and replenish axilla flora.

In order for a deodorant to work properly, it must:

A) Cling tenaciously to the skin and resist washing away with eccrine sweat,

B) Sufficiently reduce populations of diphtheroids and micrococci and their subsequent metabolic end products, and C) Mask the presence of androgen steroids (produced by bacteria) which are detectable by the human nose at a concentration of a few parts per million.

The use of natural bactericides is known in the art. For example, Kabara U.S. Pat. No. 4,002,775 and Ulrich et al. U.S. Pat. No. 4,921,694 describe lauroyl monoesters of glycerin and synergistic mixtures having antibacterial activity. Also, EP Patent Publication No. 376761, German Patent Nos. 23 54 517, 23 51 927 and 23 51 864 and United Kingdom Patent Publication No. 1,475,226 describe the deodorizing effects of lichen acid, and especially usnic acid.

SUMMARY OF THE INVENTION

According to the invention, a stick deodorant composition has active antibacterial constituents consisting essentially of natural materials, and it is essentially free of petroleum derived constituents and alcohols.

According to one aspect of the invention, in preferred embodiments, the stick deodorant composition consists essentially of the following ingredients, with the preferred ranges given by weight percent: (a) Glycerin, about 40% to 70%, preferably about 47 to 52%, and more preferably about 50%; (b) Chamomile Tea, about 20% to 60%, preferably about 32 to 36%, and more preferably about 34%; (c) Sodium Stearate, about 3% to 8%, preferably about 4.75 to 5.25%, and more preferably about 5.0%; (d) Witch Hazel, about 5% to 15%, preferably about 3.3 to 3.7%, and more preferably about 3.5%; (e) Aloe Vera, about 5% to 15%, preferably about 3.3 to 3.7%, and more preferably about 3.5%; (f) Lichen Extract, about 1% to 6%, preferably about 1.8 to 2.2%, and more preferably about 2.0%; (g) Oat Flour, about 0.1% to 3%, preferably about 1.2 to 1.3%, and more preferably about 1.25%; (h) Coriander Oil, about 0.1% to 3%, preferably about 0.38 to 0.42%, and more preferably about 0.40%; and (i) Glyceryl Monolaurate, about 0.1% to 0.6%, preferably about 0.38 to 0.42%, and more preferably about 0.40%.

According to another aspect of the invention, a stick deodorant composition has active antibacterial constituents consisting essentially of natural materials.

In preferred embodiments of this aspect of the invention, the stick deodorant composition consists essentially of the following ingredients, with the preferred ranges given by weight percent: (a) Lichen Extract, about 1% to 6%, preferably about 1.8 to 2.2%, and more preferably about 2.0%; (b) Coriander Oil, about 0.1% to 3%, preferably about 0.38 to 0.42%, and more preferably about 0.40%; and (c) Glyceryl Monolaurate, about 0.1% to 0.6%, preferably about 0.38 to 0.42%, and more preferably about 0.40%. The primary inactive constituent consists of glycerin. The composition is essentially free of petroleum derived constituents and alcohols.

These and other features and advantages of the invention will be seen from the following description of a presently preferred embodiment, and from the claims.

DESCRIPTION OF THE PRESENTLY PREFERRED EMBODIMENT(S)

The invention is a stearate based stick deodorant which contains natural antibacterial ingredients (lichen extract and coriander oil), and no petroleum derived ingredients or alcohol to provide gentle protection with minimal cause for skin irritation.

Active Constituents

The natural active constituents present in the composition of the invention include coriander oil, lichen extract, and glyceryl monolaurate. Here follows a description of the interaction of the natural active constituents in accomplishing odor prevention and the role that each constituent plays based on in vivo, in vitro observations and theoretical considerations.

The preferred formulation employs coriander, lichen extract, and glyceryl monolaurate to accomplish the tasks of the deodorant, as described above.

Coriander acts to reduce both micrococci and diphtheroids, and further serves to mask any lingering androsterone compounds. Coriander is composed mostly of oxygenated terpenoids that are weakly to moderately soluble in water. These terpenoids are, however, soluble in the phospholipid bi-layer of cell membranes and act to interfere with energy metabolism. It is understood that emulsifying terpenoids serve to enhance antimicrobial activity by increasing cell penetration potential. Coriander oil has a typical minimum inhibitory count of 0.1%, and the average zone of inhibition is 12 mm. Coriander oil is present in the formulation in a range of about 0.1 to 3 percent by weight, and preferably in a range of about 0.38 to 0.42 percent by weight.

Glyceryl monolaurate is a tranester of glycerin and the lauric acid from coconut oil. It is a gram positive specific agent and has a minimum inhibitory concentration of 0.1%, with a zone of inhibition of about 15 mm. Glyceryl monolaurate acts as an emollient, oil emulsifier, and possesses the aforementioned antibacterial qualities. It helps to enhance the efficacy of coriander by making it more water soluble, and also serves to hold the lichen extract on the skin. The antibacterial action is only a consideration when the pH of the emollient reaches the range of from 6.0 to 7.0 in the axillary vault. The pH of the invention composition is in the range from 9.0 to 10.0 and activity would not be observed until normal skin pH is restored. The composition relies more specifically on its surfactant qualities and dry feel than antibacterial potential. Glyceryl monolaurate is present in the formulation in a range of about 0.1 to 0.6 percent by weight, and preferably in a range of about 0.38 to 0.42 percent by weight.

Lichen extract also acts to reduce micrococci and diphtheroids. The active component in lichen extract is usnic acid. Usnic acid and its metal salt, sodium usnate, are potent, gram positive specific antibacterial compounds. The typical usnate content found in lichen extract is around 5.0%. A one percent level of lichen extract represents only 0.05% sodium usnate. Part for part, sodium usnate is a powerful as triclosan. Usnic acid is a dibenzofuran derivative and, in the metal salt form, it is readily soluble in water. It inhibits mitosis and cell respiration and easily permeates the cell wall of most gram positive bacteria. Due to its relatively high solubility in water, an emollient is typically provided to hold it on the skin. Sodium usnate has a typical minimum inhibitory count (MIC) of 0.002% and a minimal germicidal concentration (MGC) of 0.1%. The lichen extract would then have an MIC of 0.04 and an MGC of 2.0%. The zone of inhibition for lichen extract is about 40 mm. Lichen extract is present in the formulation in a range of about 1.0 to 6.0 percent by weight, and preferably in a range of about 1.8 to 2.2 percent by weight.

Inactive Constituents

A distinguishing factor of the invention composition from previous art is the incorporation of glycerin versus propylene glycol as the preferred humectant. While propylene glycol is antibacterial at a 10% solution level, glycerin in the composition of the invention is known to be bacteriostatic. With the potential for antibacterial enhancement aside, glycerine provides a moisturizing benefit with low skin irritation potential which is better than propylene glycol. In addition, the use of glycerin allows a break in the dependence upon petroleum derived ingredients. Glycerin is present in the formulation in a range of about 40.0 to 70.0 percent by weight, and preferably in a range of about 47.5 to 52.5 percent by weight.

Witch Hazel Distillate provides astringency without alcohol, which lessens the opportunity for skin irritation potential. Witch Hazel is present in the formulation in a range of about 5.0 to 15.0 percent by weight, and preferably in a range of about 3.3 to 3.7 percent by weight.

Aloe Vera provides soothing effects which minimize skin irritation potential. Aloe Vera is also present in the formulation in a range of about 5.0 to 15.0 percent by weight, and preferably in a range of about 3.3 to 3.7 percent by weight.

Oat Flour contributes to the texture and application of the formulation, and it also acts as an absorbent to reduce the feel of wetness. Oat Flour is present in the formulation in a range of about 0.1 to 3.0 percent by weight, and preferably in a range of about 1.2 to 1.3 percent by weight.

Sodium stearate is used as the structurant of the stick, as it is one of the least allergy-causing of the sodium salts of fatty acids. Sodium Stearate is present in the formulation in a range of about 3.0 to 8.0 percent by weight, and preferably in a range of about 4.75 to 5.25 percent by weight.

Chamomile Tea, another inactive ingredient, is present in the formulation in a range of about 20.0 to 60.0 percent by weight, and preferably in a range of about 32 to 36 percent by weight.

The composition is prepared in the form of a stick, and provides personal deodorant protection with reduced cause for skin irritation.

In one preferred embodiment, the stick deodorant composition is as follows (by weight):

| | |
|---|---|
| Glycerin | 50.00% |
| Chamomile Tea | 33.95% |
| Sodium Stearate | 5.00% |
| Witch Hazel | 3.50% |
| Aloe Vera | 3.50% |
| Lichen Extract | 2.00% |
| Oat Flour | 1.25% |
| Coriander Oil | 0.40% |
| Glyceryl Monolaurate | 0.40% |

The composition has a pH in the range of from 9.0 to 10.0.

Other embodiments are within the following claims.

What is claimed is:

1. A stick deodorant composition with active antibacterial constituents consisting essentially of (by weight based upon total weight of the composition):
   a. about 1% to 6% Lichen Extract;
   b. about 0.1% to 3% Coriander Oil; and
   c. about 0.1% to 0.6% Glyceryl Monolaurate,
said composition being essentially free of petroleum derived constituents and alcohols.

2. The stick deodorant composition of claim 1 containing Lichen Extract in the range of about 1.8% to 2.2%, by weight based upon total weight of the composition.

3. The stick deodorant composition of claim 2 containing about 2.0% by weight (based upon total weight of the composition) Lichen Extract.

4. The stick deodorant composition of claim 1 containing Coriander Oil in the range of about 0.38% to 0.42%, by weight based upon total weight of the composition.

5. The stick deodorant composition of claim 4 containing about 0.4% by weight (based upon total weight of the composition) Coriander Oil.

6. The stick deodorant composition of claim 1 containing Glyceryl Monolaurate in the range of about 0.38% to 0.42% by weight based upon total weight of the composition.

7. The stick deodorant composition of claim 6 containing about 0.40% by weight (based upon total weight of the composition) Glyceryl Monolaurate.

8. A stick deodorant composition consisting essentially of (by weight based upon total weight of the composition):
   a. about 40% to 70% Glycerin;
   b. about 20% to 60% Chamomile Tea
   c. about 3% to 8% Sodium Stearate;
   d. about 5% to 15% Witch Hazel;
   e. about 5% to 15% Aloe Vera;
   f. about 1% to 6% Lichen Extract;
   g. about 0.1% to 3% Oat Flour;
   h. about 0.1% to 3% Coriander Oil; and
   i. about 0.1% to 0.6% Glyceryl Monolaurate.

9. The stick deodorant composition of claim 8 containing Glycerin in the range of about 47% to 52%, by weight based upon total weight of the composition.

10. The stick deodorant composition of claim 9 containing about 50% by weight (based upon total weight of the composition) Glycerin.

11. The stick deodorant composition of claim 8 containing Chamomile Tea in the range of about 32% to 36%, by weight based upon total weight of the composition.

12. The stick deodorant composition of claim 11 containing about 34% by weight (based upon total weight of the composition) Chamomile Tea.

13. The stick deodorant composition of claim 8 containing Sodium Stearate in the range of about 4.75% to 5.25%, by weight based upon total weight of the composition.

14. The stick deodorant composition of claim 13 containing about 5.0% by weight (based upon total weight of the composition) Sodium Stearate.

15. The stick deodorant composition of claim 8 containing Witch Hazel in the range of about 3.3% to 3.7%, by weight based upon total weight of the composition.

16. The stick deodorant composition of claim 15 containing about 3.5% by weight (based upon total weight of the composition) Witch Hazel.

17. The stick deodorant composition of claim 8 containing Aloe Vera in the range of about 3.3% to 3.7%, by weight based upon total weight of the composition.

18. The stick deodorant composition of claim 17 containing about 3.5% by weight (based upon total weight of the composition) Aloe Vera.

19. The stick deodorant composition of claim 8 containing Lichen Extract in the range of about 1.8% to 2.2%, by weight based upon total weight of the composition.

20. The stick deodorant composition of claim 19 containing about 2.0% by weight (based upon total weight of the composition) Lichen Extract.

21. The stick deodorant composition of claim 8 containing Oat Flour in the range of about 1.2% to 1.3%, by weight based upon total weight of the composition.

22. The stick deodorant composition of claim 21 containing about 1.25% by weight (based upon total weight of the composition) Oat Flour.

23. The stick deodorant composition of claim 8 containing Coriander Oil in the range of about 0.38% to 0.42%, by weight based upon total weight of the composition.

24. The stick deodorant composition of claim 23 containing about 0.40% by weight (based upon total weight of the composition) Coriander Oil.

25. The stick deodorant composition of claim 8 containing Glyceryl Monolaurate in the range of about 0.38% to 0.42%, by weight based upon total weight of the composition.

26. The stick deodorant composition of claim 25 containing about 0.40% by weight (based upon total weight of the composition) Glyceryl Monolaurate.

* * * * *